(12) United States Patent
Pevere et al.

(10) Patent No.: US 6,525,225 B2
(45) Date of Patent: Feb. 25, 2003

(54) PROCESS FOR PREPARING DIKETONE COMPOUNDS AND PRECURSORS THERETO

(75) Inventors: Virginie Pevere, Lyons (FR); Alain Gadras, Lyons (FR); Susan Mary Cramp, Ongar (GB); Charles Walter Ellwood, Ongar (GB)

(73) Assignee: Rhone Poulenc Agrochimie, Lyons (FR)

( * ) Notice: Subject to any disclaimer, the term of this patent is extended or adjusted under 35 U.S.C. 154(b) by 0 days.

(21) Appl. No.: 09/990,282

(22) Filed: Nov. 23, 2001

(65) Prior Publication Data

US 2002/0062045 A1 May 23, 2002

Related U.S. Application Data

(60) Continuation of application No. 09/811,487, filed on Mar. 20, 2001, which is a division of application No. 09/117,372, filed as application No. PCT/EP97/00370 on Jan. 28, 1997, now Pat. No. 6,235,942.

(30) Foreign Application Priority Data

Feb. 1, 1996 (EP) .............................. 96300718

(51) Int. Cl.$^7$ ............................................ C07C 321/28
(52) U.S. Cl. .......................................... 568/43; 568/42
(58) Field of Search ........................ 568/38, 39, 42, 568/43

(56) References Cited

U.S. PATENT DOCUMENTS

| | | | |
|---|---|---|---|
| 2,763,692 A | 9/1956 | Gregory | 260/592 |
| 3,882,104 A | 5/1975 | Grisar et al. | 260/240 |
| 3,954,871 A | 5/1976 | Buu-Hoi | 260/570.6 |
| 4,482,745 A | 11/1984 | Maulding | 568/314 |
| 4,670,445 A | 6/1987 | Spitzer | 514/300 |
| 4,966,998 A | 10/1990 | Lee | 562/869 |
| 5,015,777 A | 5/1991 | Chisolm | 568/314 |
| 5,334,753 A | 8/1994 | Bennetau et al. | 562/405 |
| 5,344,992 A | 9/1994 | Drewes | 568/314 |
| 5,366,957 A | 11/1994 | Cain et al. | 504/271 |
| 5,371,064 A | 12/1994 | Cramp et al. | 504/271 |
| 5,656,573 A | 8/1997 | Roberts et al. | 504/271 |
| 6,096,929 A | 8/2000 | Boaz | 568/316 |

FOREIGN PATENT DOCUMENTS

| | | |
|---|---|---|
| DE | 2047028 | 4/1971 |
| DE | 2418480 | 11/1974 |
| DE | 2441498 | 3/1975 |
| DE | 2451566 | 5/1975 |
| DE | 3836161 | 4/1990 |
| EP | 0154494 | 9/1985 |
| EP | 0195247 | 9/1986 |
| EP | 0418175 | 3/1991 |
| EP | 0487357 | 5/1992 |
| EP | 0507013 | 10/1992 |
| EP | 0524018 | 1/1993 |
| EP | 0527036 | 2/1993 |
| EP | 0560482 | 9/1993 |
| EP | 0580439 | 1/1994 |
| EP | 0609798 | 8/1994 |
| GB | 1321701 | 6/1973 |
| GB | 1435639 | 5/1976 |
| GB | 1475890 | 6/1977 |
| WO | 93/13060 | 7/1993 |
| WO | 94/18179 | 8/1994 |

OTHER PUBLICATIONS

Aliev et al, *Sulfur Lett.*, vol. 12, No. 3, pp. 123–132 (1991), published by Harwood Academic Publishers GmbH, London, UK.

Crow et al, *Aust. J. Chem.*, vol. 32, No. 1, pp. 123–131 (1979), published by Commonwealth Scientific and Industrial Research Organization, Melbourne, Australia.

Comins et al, *Tetrahedron Lett.*, vol. 24, No. 49, pp. 5465–5468 (1983), published by Pergamon Press, Oxford, UK.

Ruwet et al, *Bull. Soc. Chim. Belg.*, vol. 78, No. 9–10, pp. 571–582 (1969), published by Societé chimique de Belgique, Brussels, Belgium.

(List continued on next page.)

*Primary Examiner*—Jean F. Vollano
(74) *Attorney, Agent, or Firm*—Burns, Doane, Swecker & Mathis, L.L.P.

(57) ABSTRACT

A process for preparing compounds of the formula:

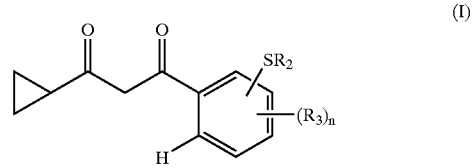

(I)

wherein $R_2$ is lower alkyl; or phenyl optionally substituted by from one to five groups, the same or different, which are lower alkyl, lower haloalkyl, halogen or —$SR_4$; $R_3$ is halogen, lower alkyl, lower haloalkyl, lower alkoxy, lower haloalkoxy, —S-alkyl, cycloalkyl having from 3 to 7 carbon atoms in the ring, alkenyl or alkynyl having from 3 to 7 carbon atoms, or —$(CR_5R_6)_q$—$SR_2$ wherein q is one or two; $R_4$ is lower alkyl; $R_5$ and $R_6$ independently represent hydrogen, lower alkyl or lower haloalkyl; and n is zero or an integer from one to three; intermediate compounds of the formula:

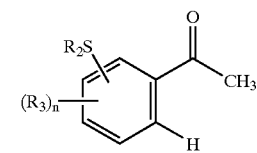

(II)

and processes for preparing them.

65 Claims, No Drawings

OTHER PUBLICATIONS

Buu–Hoi et al, *Chimie Therapeutique*, vol. 2, No. 1, pp. 39–48 (1967), published by Société Edifor., Paris, France.

Shargi et al, *J. Chem. Eng. Data*, vol. 8, No. 2, pp. 276–278 (1963), published by American Chemical Society, Washington, D.C.

*Chemical Abstracts*, vol. 90, No. 3, abstract No. 22614p (1979), published by American Chemical Society, Columbus, Ohio.

Julia et al, *Tetrahedron*, vol. 47, No. 34, pp. 6939–6950 (1991), published by Pergamon Press, Oxford, UK.

*Chemical Abstracts*, vol. 112, No. 1, abstract No. 7509n (1990), published by American Chemical Society, Columbus Ohio.

*Chemical Abstracts*, vol. 85, abstract No. 105335 (1976) [abstract of Henrick et al, *J. Agric Food Chem*, 24(5), pp. 1023–1029 (1976)], published by American Chemical Society, Columbus, Ohio.

March, *Advanced Organic Chemistry*, p. 368 (1968), published by McGraw–Hill Book Company, New York, New York.

CA:110:23464 abs of *Tetrahedron* by Dieter et al 44(7), pp. 1915–1924 (1988).

CA:115:135931 abs of CA2027169 (Oct. 1991).

CA:67:32435 ab of *Chim Ther* by Buu–Hoi et al, 2(1), pp. 39–48 (1967).

CA:92:128853 abs of *Collect Czech Chem Commun* by Valenta et al, 44(9), pp. 2677–2688 (1979).

CA:86:139268 abs of *J Am Chem Soc* by Martin et al, 99(1), pp. 152–162 (1977).

CA:108:56064 abs of *Collect Czech Chem Commun* by Valenta et al, 52 (4), pp. 1062–1072 (1987).

CA:109:230716 abs of *Synthesis* by Singh et al, 10, pp. 873–875 (1987).

CA:115:232151 abs of *Tetrahedron* by Julia et al, 47(34), pp. 6939–6950 (1991).

CA:117:90296 abs of WO 9206085 (Apr. 1992).

CA:107:115558 abs of *Collect Czech Chem Commun* by Protiva et al 51 (11) (1986).

CA:107:236492 abs of *Collect Czech Chem Comun* by Kmonicek et al, 52(3), pp. 793–803 (1987).

PROCESS FOR PREPARING DIKETONE COMPOUNDS AND PRECURSORS THERETO

CROSS-REFERENCE TO RELATED APPLICATIONS

This application is a continuation of U.S. application Ser. No. 09/811,487, filed Mar. 20, 2001, which is a divisional of U.S. patent application Ser. No. 09/117,372, filed Oct. 28, 1998, now U.S. Pat. No. 6,235,942, issued May 22, 2001, which is the U.S. national stage of International Patent Application No. PCT/EP97/00370, filed Jan. 28, 1997 and designating the United States, and published by the International Bureau in English on Aug. 7, 1997 as WO 97/28122. The disclosures of U.S. application Ser. Nos. 09/811,487 and 09/117,372 are herein incorporated by reference.

BACKGROUND OF THE INVENTION

This invention relates to a process for preparing ketone compounds and the products obtained by this process. More particularly, the invention relates to the preparation of intermediate compounds in the manufacture of pesticides.

Pesticidal 4-benzoylisoxazoles, particularly 5-cyclopropylisoxazole herbicides and intermediate compounds in their synthesis, are described in the literature, for example in European Patent Publication Nos. 0418175, 0487357, 0527036, 0560482, 0609798 and 0682659.

Various methods for preparing these compounds are known. It is an object of the present invention to provide improved methods for the preparation of these compounds and the intermediate compounds thereto.

SUMMARY OF THE INVENTION

According to a first aspect of the invention, there is provided a process for the preparation of a compound of formula (I) by the reaction of a compound of formula (II) with a compound of formula (III), according to the reaction scheme Sc1 indicated below:

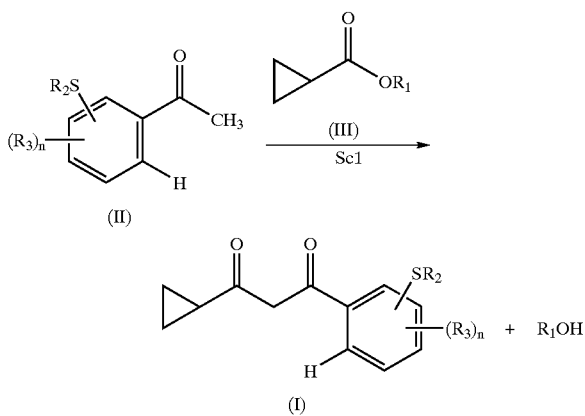

wherein:

$R_1$ is lower alkyl;

$R_2$ is lower alkyl; or phenyl optionally substituted by from one to five groups which may be the same or different selected from lower alkyl, lower haloalkyl, halogen and —$SR_4$;

$R_3$ is halogen, lower alkyl, lower haloalkyl, lower alkoxy, lower haloalkoxy, —S-alkyl, cycloalkyl having from 3 to 7 ring carbon atoms, alkenyl or alkynyl having from 3 to 7 carbon atoms, or —$(CR_5R_6)_q$—$SR_2$ wherein q is one or two;

n is zero or an integer from one to three;

$R_4$ is lower alkyl;

and $R_5$ and $R_6$ independently represent hydrogen, lower alkyl or lower haloalkyl.

According to a second aspect of the present invention, there is provided a process for the preparation of a compound of formula (II) by the reaction of a compound of formula (V) with a mercaptan of formula (IV), optionally present in the form of the thiolate, according to reaction scheme Sc2 indicated below:

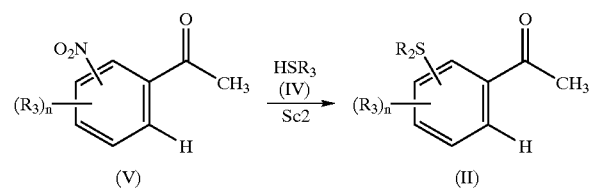

wherein $R_2$, $R_3$ and n in formulae (II) and (V) have the same meanings as given before in reaction scheme Sc1. The group —$NO_2$ is generally present in the 2- or 4-position, preferably the 2-position of the phenyl ring.

According to a third aspect of the invention there is provided a process for the preparation of a compound of formula (V) by the reaction of a compound of formula (VII) or (VI), as well as a process for the preparation of a compound of formula (VI) from a compound of formula (VII), according to the reaction scheme Sc3 indicated below:

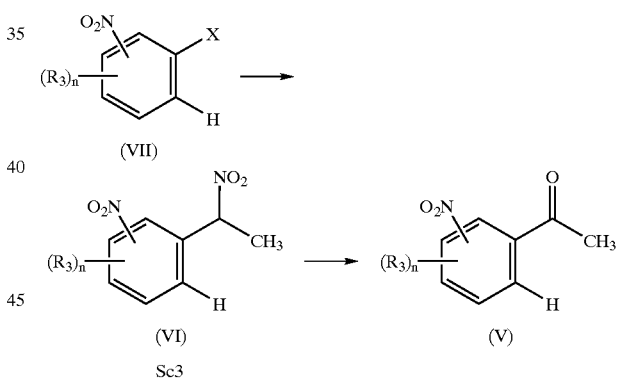

wherein $R_3$ and n have the same meanings as in reaction schemes Sc2 and Sc1, and X represents halogen, preferably chlorine or fluorine. Preferably, the group —$NO_2$ in formula (VII) is in the 2- or 4-position, most preferably in the 2-position of the phenyl ring.

Certain intermediate compounds of formula (II) are novel and as such constitute a further feature of the present invention, in particular 2-methylthio-4-trifluoromethylacetophenone and 3,4-dichloro-2-(methylthio)acetophenone.

DETAILED DESCRIPTION OF THE INVENTION

The compounds of formula (I) and a number of processes for their preparation have been described in the European Patent Applications cited above.

By the term "lower" is meant radicals comprising at least one hydrocarbon chain, it being understood that such radicals contain from one to six carbon atoms linked together in a straight- or branched-carbon chain.

Preferably, $R_1$ and $R_2$ are lower alkyl (most preferably, methyl).

Preferably, the group —$SR_2$ occupies the 2-, 3- or 4-position of the phenyl ring (most preferably, the 2-position).

Preferably, n is one or two.

The reaction generally proceeds in better yield when a group $R_3$ is not halogen in the 2-position of the phenyl ring.

Preferably, $R_3$ is halogen or trifluoromethyl. More preferably, $(R_3)_n$ is 4-$CF_3$ or 3,4-dichloro.

The compounds of formula (III) above used in Scheme Sc1 are known in the literature and their preparation has been expressly described in the prior art known to the skilled worker. Some references particularly pertinent to the preparation of this reagent may be found by the skilled worker in various sources of chemical literature, including *Chemical Abstracts* and information databases available to the public.

The preparation of compounds of formula (I) using compounds of formula (II) and (III) according to scheme Sc1 above may be preferably effected in a polar or a polar aprotic solvent. Examples of polar aprotic solvents include dimethylsulfoxide, dimethylformamide, N,N-dimethylacetamide, N-methylpyrrolidone, a compound of formula (III); an ether compound, particularly dioxane and tetrahydrofuran; or an aromatic or aliphatic halogenated hydrocarbon, particularly chlorobenzenes. Examples of apolar aprotic solvents include aromatic or aliphatic hydrocarbons, particularly toluene and xylenes.

Generally, the reaction temperature used in Sc1 above is from 0° C. to the boiling point of the solvent, preferably, between 0° C. and 100° C. Generally the Sc1 reaction takes place in the presence of a strong base, which is most preferably selected from an alkoxide of an alkali or alkaline earth metal, notably sodium ethoxide, sodium methoxide, sodium or potassium t-butoxide; and a metal hydride (notably sodium hydride).

According to a preferred variant of the process of Sc1 of the present invention, the reaction is performed with continuous distillation of the alcohol $R_1$—OH formed in the course of the reaction, at atmospheric pressure or under reduced pressure (preferably from 1 to 20% below atmospheric pressure). Optionally, the alcohol $R_1$—OH formed may be removed by the use of a suitable molecular sieve, for example a 4 Angstrom molecular sieve.

Compounds of formula $HSR_2$ used in reaction scheme Sc2 are known in the literature and their preparations are expressly described in the prior art known to the skilled worker. The references particularly pertinent to the preparation of this reagent may be found by the skilled worker in various sources of classical chemistry including *Chemical Abstracts* and information databases available to the public. The salts or thiolates derived from the compound of formula (IV) may be prepared by means known to the skilled worker. These thiolates are preferably alkaline salts, particularly sodium or potassium thiolate.

The preparation of compounds of formula (II) according to scheme Sc2 from the acetophenone of formula (V) and a compound of formula (IV) is preferably performed in a solvent of the compound of formula (IV) which may be inert to the reaction conditions. Examples of other suitable solvents include sulfoxides such as dimethylsulfoxide; amides such as dimethylformamide, N,N-dimethylacetamide and N-methylpyrrolidone; ketones such as acetone and methyl isobutyl ketone; ether solvents, particularly dioxane and tetrahydrofuran; aromatic, aliphatic and cycloaliphatic hydrocarbons and halogenated or non-halogenated hydrocarbons, particularly chlorobenzene, dichloromethane and toluene. The presence of a small quantity of water is also acceptable in allowing the solubilization of the thiolate.

When the reaction according to scheme Sc2 takes place using a compound of formula (IV) in the form of the mercaptan and not in the form of a thiolate salt, the reaction is preferably effected in the presence of a base such as a hydroxide of an alkali metal or alkali earth metal (preferably, sodium or potassium), or a carbonate or hydride (such as sodium hydride). The reaction may also be performed using various forms of catalyst, particularly phase transfer catalysts such as a quaternary ammonium salt, for example, tetrabutylammonium bromide.

The two reactions which comprise together the reaction scheme Sc3 above are generally distinct but preferably they may occur in succession. That is, the compounds of formula (V) may be prepared from the compounds of formula (VII) via an intermediate of formula (VI) which may be isolated or used in situ in the course of the reaction.

The reaction conditions for the preparation of the compound of formula (V) from the compound of formula (VI) are known in the art and described in the literature, notably by J. G. Reid and J. M. Reny Runge in *Tetrahedron Letters*, Vol. 31 (1990), pp. 1093–1096; G. A. Olah et al. *Synthesis* (1980), pp. 662–663; N. Kornblum et al, *J. Org. Chem.*, Vol. 47 (1982), pp. 4534–38; S. Chandrasekaran et al, *Synthetic Communications*, Vol. 17 (1987), pp. 195–201.

The invention is thus also concerned with the preparation of compounds of formula (VI) from compounds of formula (VII) by the reaction of nitroethane in the presence of a base in a solvent which is selected from a compound of formula (VII), nitroethane, a solvent inert to the reaction conditions, and the base being selected from an hydroxide, a carbonate, a hydride, an alkoxide of an alkaline metal or an alkaline earth metal, and guanidine. An advantage of this aspect of the present invention is that relatively simple bases may be used in the reaction scheme Sc3.

Solvents suitable for use in preparing compounds (VI) from compounds (VII) include nitroethane itself (used in excess compared to the quantity normally used as a reactant); aromatic or aliphatic halogenated or non-halogenated hydrocarbons, particularly chlorobenzene; aromatic or aliphatic hydrocarbons, particularly toluene and xylenes; polar aprotic solvents such as dimethylsulfoxide, dimethylformamide, N,N-dimethylacetamide, N-methylpyrrolidone; acetonitrile; ether solvents, particularly dioxane and tetrahydrofuran. The presence of a small quantity of water is also acceptable in allowing the solubilization of the reaction mixture, while not reacting with the reactants themselves.

The reaction temperature for converting (VII) to (VI) is generally from 0° C. to 50° C. The reaction may also be carried out in an aqueous or non-aqueous medium. Among the bases suitable for the use in this process, one may cite hydroxides or carbonates of alkali metals or alkaline earth metals, preferably sodium or potassium, sodium carbonate, potassium carbonate or cesium carbonate; or tetramethylguanidine. These bases may be used alone or in mixture with others. The reaction may also be conveniently performed using various types of catalyst, particularly phase transfer catalysts such as a quaternary ammonium salt, for example, tetrabutylammonium bromide.

The following non-limiting examples illustrate the invention.

EXAMPLE 1

Preparation of 1-cyclopropyl-3-(2-methylthio-4-trifluoromethylphenyl)propane-1,3-dione (Reaction Scheme Sc1)

In a reaction vessel under an inert atmosphere, one adds 1.15 g of sodium methoxide and 22 ml of toluene. This is heated to 80° C. at a pressure of 400 mbars. A mixture of 3.3 ml of methyl cyclopropylcarboxylate and 3.8 g of 2-methylthio-4-trifluoromethylacetophenone in 6 ml of anhydrous toluene is added over 3 hours with constant distillation of methanol formed. The reaction is stirred for one hour at 80° C. The reaction is then cooled and the diketone precipitated in a mixture of 80 ml of ice water containing 0.75 ml of concentrated sulfuric acid. The organic phase is retained, washed with water and the toluene removed under reduced pressure to give 3.67 g of 1-cyclopropyl-3-(2-methylthio-4-trifluoromethylphenyl)propane-1,3-dione in the form of an orange powder, m.p. 64° C. Yield=75%.

By proceeding in a similar manner, but heating at a temperature of 70° C. and a pressure of 230 mbars, 3-(4-chloro-2-methylthiophenyl)-1-cyclopropylpropan-1,3-dione was prepared in 98% yield (purity greater than 80%). This compound was also similarly prepared wherein the reaction took place at a temperature of 70° for 6.5 hours and in the presence of 4 Angstrom molecular sieves in place of constant distillation of the methanol formed.

EXAMPLE 2

Preparation of 1-cyclopropyl-3-[3,4-dichloro-2-(methylthio)phenyl]propane-1,3-dione (Reaction Scheme Sc1)

Sodium hydride (0.178 g, 60% oil dispersion, 0.0045 M) is suspended in tetrahydrofuran (1.8 ml), stirred and heated at reflux while a solution of a mixture of methyl cyclopropanecarboxylate (0.42 g, 0.0042M) and 3,4-dichloro-2-(methylthio)acetophenone (0.5 g, 0.0021M) in tetrahydrofuran (3 ml) is added.

The mixture is stirred and heated at reflux for 3.5 hours, then cooled and poured onto saturated aqueous sodium bicarbonate. The mixture is then extracted with ether, washed with brine, dried over magnesium sulfate, filtered and evaporated to give a gum (which is purified by dry column flash chromatography eluted with ethyl acetate in cyclohexane to give 3-cyclopropyl-1-[3,4-dichloro-2-(methylthio)phenyl]propane-1,3-dione (0.35 g, 55%) as a yellow oil.

EXAMPLE 3

Preparation of 2-methylthio-4-trifluoromethylacetophenone (Reaction Scheme Sc2)

To 0.15 g of 2-nitro-4-trifluoromethylacetophenone diluted in 0.5 ml of acetone is added 0.256 g of an aqueous solution of 21% wt/wt sodium thiomethoxide and the mixture is stirred for five hours at 20° C. The aqueous phase is separated, then removed, then 2 ml of water are added and the acetone removed under reduced pressure. The mixture is then treated with dichloromethane and the aqueous phase removed. The organic phase is washed with fresh water, then the solvent is evaporated under reduced pressure to obtain 0.085 g of 2-methylthio-4-trifluoromethylacetophenone with a melting point of 71° C.

By proceeding in a similar manner, 3,4-dichloro-2-(methylthio)acetophenone may be prepared, $^1$H NMR (CDCl$_3$) 2.4 (s,3H), 2.6 (s,3H), 7.15 (d,1H), 7.5 (d,1H).

EXAMPLE 4

Preparation of 1-(2-nitro-4-trifluoromethylphenyl)-1-nitroethane (Reaction Scheme Sc3)

0.87 g of sodium carbonate in 5 ml of anhydrous toluene are placed in a 30 ml reaction vessel, and 0.11 g of benzyltriethylammonium chloride and 1.13 g of 4-chloro-3-nitrobenzotrifluoride and 0.38 g of nitroethane are added at the same time. The mixture is stirred for 16 hours at 20° C., 10 ml of water are added and the aqueous phase is separated, then acidified by a 4N solution of sulfuric acid. It is then extracted with 5 ml of methyl t-butyl ether. After removing the organic solvent, 0.18 g of a mixture is obtained which is separated by column chromatography using reverse phase silica eluting with a mixture of water and acetonitrile to obtain 0.12 g of the title compound, m.p. 48° C.

What is claimed is:

1. The compound which is 2-methylthio-4-trifluoromethylacetophenone or 3,4-dichloro-2-(methylthio)acetophenone.

2. A compound of the formula (II):

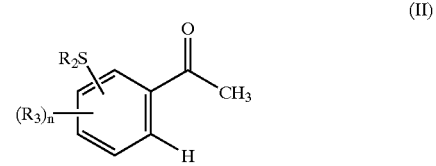

(II)

wherein:
  $SR_2$ is in the two position of the phenyl ring;
  $R_2$ is $C_1$ alkyl, $C_2$ alkyl or $C_3$ alkyl;
  $R_3$ is halogen, lower haloalkyl, lower alkoxy, lower haloalkoxy, —S-alkyl, cycloalkyl having from 3 to 7 carbon atoms in the ring, alkenyl or alkynyl having from 3 to 7 carbon atoms, or —(CR$_5$R$_6$)$_q$—SR$_2$' wherein R$_2$' is lower alkyl; or phenyl which is unsubstituted or is substituted by from one to five groups which are the same or different selected from the group consisting of lower alkyl, lower haloalkyl, halogen and —SR$_4$; and q is one or two;
  $R_4$ is lower alkyl;
  $R_5$ and $R_6$ independently represent hydrogen, lower alkyl or lower haloalkyl;
  and n is an integer from one to three.

3. A compound of the formula (II):

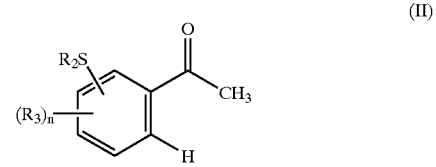

(II)

wherein:
  $R_2$ is lower alkyl; or phenyl which is unsubstituted or is substituted by from one to five groups which are the same or different selected from the group consisting of lower alkyl, lower haloalkyl, halogen and —SR$_4$;
  $(R_3)_n$ is 4-trifluoromethyl or 3,4-dichloro;
  and $R_4$ is lower alkyl.

4. A compound of the formula (II):

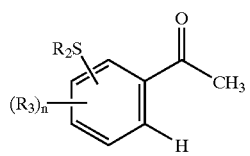

wherein:
$R_2$ is lower alkyl;
$R_3$ is halogen or trifluoromethyl; and
n is 1.

5. A compound according to claim 2, wherein $R_2$ is methyl.

6. A compound according to claim 2, wherein n is 1 or 2.

7. A compound according to claim 2, wherein $R_3$ is halogen or trifluoromethyl.

8. A compound according to claim 2, wherein $(R_3)_n$ is 3,4-dichloro or 4-trifluoromethyl.

9. A compound according to claim 2, wherein $(R_3)_n$ is 3,4-dichloro.

10. A compound according to claim 2, wherein $(R_3)_n$ is 4-trifluoromethyl.

11. A compound according to claim 3, wherein the $SR_2$ group is in the 2,3 or 4 position of the phenyl ring.

12. A compound according to claim 3, wherein the $SR_2$ group is in the 2 position of the phenyl ring.

13. A compound according to claim 3, wherein $R_2$ is lower alkyl.

14. A compound according to claim 3, wherein $R_2$ is methyl.

15. A compound according to claim 3, wherein $(R_3)_n$ is 3,4-dichloro.

16. A compound according to claim 3, wherein $(R_3)_n$ is 4-trifluoromethyl.

17. A compound according to claim 4, wherein $R_3$ is trifluoromethyl.

18. A process for preparing a compound of formula (II) which comprises reacting a compound of formula (V) with a mercaptan $HSR_2$ of formula (IV) according to reaction scheme Sc2 indicated below:

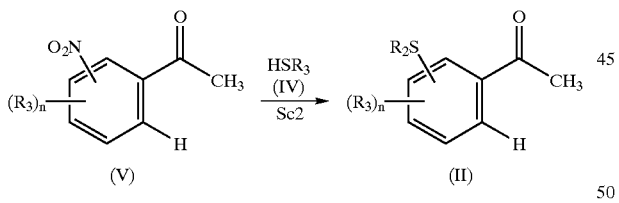

wherein:
$SR_2$ is in the two position of the phenyl ring;
$R_2$ is $C_1$ alkyl, $C_2$ alkyl or $C_3$ alkyl;
$R_3$ is halogen, lower haloalkyl, lower alkoxy, lower haloalkoxy, —S-alkyl, cycloalkyl having from 3 to 7 carbon atoms in the ring, alkenyl or alkynyl having from 3 to 7 carbon atoms, or —$(CR_5R_6)_q$—$SR_2$' wherein $R_2$' is lower alkyl; or phenyl which is unsubstituted or is substituted by from one to five groups which are the same or different selected from the group consisting of lower alkyl, lower haloalkyl, halogen and —$SR_4$; and q is one or two;
$R_4$ is lower alkyl;
$R_5$ and $R_6$ independently represent hydrogen, lower alkyl or lower haloalkyl;
and n is zero or an integer from one to three.

19. A process according to claim 18, wherein the reactant of formula (IV) is employed as solvent.

20. A process according to claim 19, wherein the compound of formula (IV) is in the form of a mercaptan, and the reaction is performed in the presence of a base.

21. A process according to claim 20, wherein the base is a hydroxide of an alkali metal or alkali earth metal, or a carbonate or hydride.

22. The process according to claim 18, carried out in the presence of a catalyst.

23. The process according to claim 22, wherein the catalyst is a phase transfer catalyst.

24. The process according to claim 23, wherein the phase transfer catalyst is a quaternary ammonium salt.

25. The process according to claim 19, carried out in the presence of a catalyst.

26. The process according to claim 25, wherein the catalyst is a phase transfer catalyst.

27. The process according to claim 26, wherein the phase transfer catalyst is a quaternary ammonium salt.

28. The process according to claim 20, carried out in the presence of a catalyst.

29. The process according to claim 28, wherein the catalyst is a phase transfer catalyst.

30. The process according to claim 29, wherein the phase transfer catalyst is a quaternary ammonium salt.

31. The process according to claim 21, carried out in the presence of a catalyst.

32. The process according to claim 31, wherein the catalyst is a phase transfer catalyst.

33. The process according to claim 32, wherein the phase transfer catalyst is a quaternary ammonium salt.

34. A process for preparing a compound of formula (II) which comprises reacting a compound of formula (V) with a mercaptan $HSR_2$ of formula (IV) according to reaction scheme Sc2 indicated below:

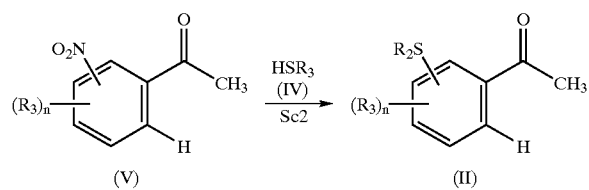

wherein:
$R_2$ is lower alkyl; or phenyl which is unsubstituted or is substituted by from one to five groups which are the same or different selected from the group consisting of lower alkyl, lower haloalkyl, halogen and —$SR_4$;
$(R_3)_n$ is 4-trifluoromethyl or 3,4-dichloro;
and $R_4$ is lower alkyl.

35. A process according to claim 34, wherein the reactant of formula (IV) is employed as solvent.

36. A process according to claim 35, wherein the compound of formula (IV) is in the form of a mercaptan, and the reaction is performed in the presence of a base.

37. A process according to claim 36, wherein the base is a hydroxide of an alkali metal or alkali earth metal, or a carbonate or hydride.

38. The process according to claim 34, carried out in the presence of a catalyst.

39. The process according to claim 38, wherein the catalyst is a phase transfer catalyst.

40. The process according to claim 39, wherein the phase transfer catalyst is a quaternary ammonium salt.

41. The process according to claim 35, carried out in the presence of a catalyst.

42. The process according to claim 41, wherein the catalyst is a phase transfer catalyst.

43. The process according to claim 42, wherein the phase transfer catalyst is a quaternary ammonium salt.

44. The process according to claim 36, carried out in the presence of a catalyst.

45. The process according to claim 44, wherein the catalyst is a phase transfer catalyst.

46. The process according to claim 45, wherein the phase transfer catalyst is a quaternary ammonium salt.

47. The process according to claim 37, carried out in the presence of a catalyst.

48. The process according to claim 47, wherein the catalyst is a phase transfer catalyst.

49. The process according to claim 48, wherein the phase transfer catalyst is a quaternary ammonium salt.

50. A process for preparing a compound of formula (II) which comprises reacting a compound of formula (V) with a mercaptan $HSR_2$ of formula (IV) according to reaction scheme Sc2 indicated below:

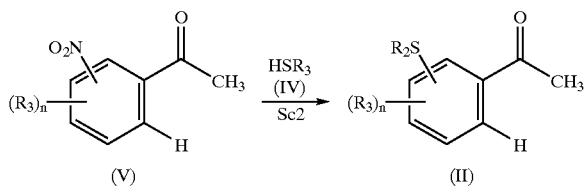

wherein:
$R_2$ is lower alkyl;
$R_3$ is halogen or trifluoromethyl; and
n is 1.

51. A process according to claim 50, wherein the reactant of formula (IV) is employed as solvent.

52. A process according to claim 51, wherein the compound of formula (IV) is in the form of a mercaptan, and the reaction is performed in the presence of a base.

53. A process according to claim 52, wherein the base is a hydroxide of an alkali metal or alkali earth metal, or a carbonate or hydride.

54. The process according to claim 53, carried out in the presence of a catalyst.

55. The process according to claim 54, wherein the catalyst is a phase transfer catalyst.

56. The process according to claim 55, wherein the phase transfer catalyst is a quaternary ammonium salt.

57. The process according to claim 51, carried out in the presence of a catalyst.

58. The process according to claim 57, wherein the catalyst is a phase transfer catalyst.

59. The process according to claims 58, wherein the phase transfer catalyst is a quaternary ammonium salt.

60. The process according to claim 52, carried out in the presence of a catalyst.

61. The process according to claim 60, wherein the catalyst is a phase transfer catalyst.

62. The process according to claim 61, wherein the phase transfer catalyst is a quaternary ammonium salt.

63. The process according to claim 53, carried out in the presence of a catalyst.

64. The process according to claim 63, wherein the catalyst is a phase transfer catalyst.

65. The process according to claim 64, wherein the phase transfer catalyst is a quaternary ammonium salt.

* * * * *